(12) United States Patent
Horton

(10) Patent No.: US 8,304,376 B2
(45) Date of Patent: Nov. 6, 2012

(54) BIODEGRADABLE WIPE UTILIZING BIO-BASED LUBRICANT

(75) Inventor: Cathy Horton, South Russell, OH (US)

(73) Assignee: Hoover, Inc., Glenwillow, OH (US)

( * ) Notice: Subject to any disclaimer, the term of this patent is extended or adjusted under 35 U.S.C. 154(b) by 0 days.

(21) Appl. No.: 13/281,756

(22) Filed: Oct. 26, 2011

(65) Prior Publication Data
US 2012/0042900 A1 Feb. 23, 2012

Related U.S. Application Data

(63) Continuation of application No. 12/782,254, filed on May 18, 2010, now Pat. No. 8,071,524.

(60) Provisional application No. 61/179,531, filed on May 19, 2009, provisional application No. 61/179,363, filed on May 18, 2009.

(51) Int. Cl.
*C11D 3/382* (2006.01)
*C11D 3/44* (2006.01)

(52) U.S. Cl. ........ 510/295; 510/130; 510/251; 510/254; 510/432; 510/189; 510/317; 510/417

(58) Field of Classification Search ............... 510/130, 510/295, 189, 251, 371, 417, 432, 254
See application file for complete search history.

(56) References Cited

U.S. PATENT DOCUMENTS

| 5,340,495 | A | 8/1994 | Mulcahy et al. | |
|---|---|---|---|---|
| 5,980,922 | A | 11/1999 | Mackey et al. | |
| 6,440,437 | B1 | 8/2002 | Krzysik et al. | |
| 6,462,011 | B1 | 10/2002 | Collins et al. | |
| 6,613,729 | B1 | 9/2003 | Cole et al. | |
| 2002/0031966 | A1 | 3/2002 | Tomarchio et al. | |
| 2002/0111283 | A1* | 8/2002 | Argentieri et al. | 510/167 |
| 2004/0092417 | A1 | 5/2004 | Moodycliffe et al. | |
| 2005/0159063 | A1 | 7/2005 | Hill et al. | |
| 2006/0062832 | A1* | 3/2006 | Lopes | 424/443 |
| 2006/0276356 | A1 | 12/2006 | Panandiker et al. | |
| 2006/0293214 | A1* | 12/2006 | Cheng et al. | 510/504 |
| 2007/0037721 | A1 | 2/2007 | Michels et al. | |
| 2007/0082033 | A1* | 4/2007 | Doerschner et al. | 424/443 |
| 2008/0069785 | A1* | 3/2008 | Jones | 424/59 |
| 2008/0279792 | A1* | 11/2008 | Eitrich et al. | 424/59 |
| 2009/0197819 | A1* | 8/2009 | Johnson et al. | 514/23 |

OTHER PUBLICATIONS

United States Patent Office Action for U.S. Appl. No. 13/281,756 dated Nov. 26, 2010 (8 pages).
United States Patent Office Notice of Allowance for U.S. Appl. No. 13/281,756 dated Jul. 22, 2011 (6 pages).

* cited by examiner

*Primary Examiner* — Charles Boyer

(74) *Attorney, Agent, or Firm* — Michael Best & Friedrich LLP

(57) ABSTRACT

The present invention generally relates to a biodegradable lubricating wipe, such as wet wipes. The wet wipes typically being fibrous sheet materials, pre-moistened with a solution for improved lubrication and/or protection of an area. In one embodiment the solution is comprised of a bio-based lubricant, a bio-based solvent and water. In one embodiment, the solution is comprised of mineral spirits and refined soybean oil. In another embodiment the solution is comprised of soy methyl ester and refined soybean oil. In yet another embodiment, the fibrous sheet material of the invention is biodegradable and the solution portion breaks down into a vaporizing component and a biodegradable carrier portion.

25 Claims, No Drawings

BIODEGRADABLE WIPE UTILIZING BIO-BASED LUBRICANT

RELATED APPLICATION DATA

This application claims priority to U.S. Provisional Patent Application No. 61/179,363, filed on May 18, 2009 and U.S. Provisional Patent Application No. 61/179,531, filed on May 19, 2009. The above-identified patent applications are hereby incorporated herein by reference in their entirety.

FIELD OF THE INVENTION

The present invention generally relates to a biodegradable lubricating wipe, such as wet wipes. The wet wipes typically being fibrous sheet materials, pre-moistened with a solution for improved lubrication and/or protection of an area. In one embodiment the solution is comprised of a bio-based lubricant, a bio-based solvent and water. In one embodiment, the solution is comprised of mineral spirits and refined soybean oil. In another embodiment the solution is comprised of soy methyl ester and refined soybean oil. In yet another embodiment, the fibrous sheet material of the invention is biodegradable and the solution portion breaks down into a vaporizing component and a biodegradable carrier portion.

BACKGROUND OF INVENTION

Wet wipes have long been used as a carrier for a variety of chemicals, enzymes and liquids. The wipe substrate typically being a fiber or paper based means capable of holding or containing a liquid. Typically the wet wipe is stored in a storage means which aids in the retention of the chemical (i.e., prevents the wipe from drying out). Once removed from the storage means, the wet wipe can be applied to a variety of surfaces. The most popularly used and known wet wipe is a stack of moistened sheets packaged in a plastic container. Wet wipes have been made form a variety of materials moistened with a variety of suitable wiping solutions. Typically the wet wipes have been available in folded or unfolded configurations. As one skilled in the art would recognize, wet wipes can be folded in configurations including c-folds, z-folds or quarter folds. In some configurations the wet wipe is interfolded with the wet wipe immediately above or preceding. In another configuration the wet wipes have the form of continuous webs of material which include perforations to separate the individual wet wipes and which can be wound into rolls or packaged in plastic containers. Examples of these wipes include baby wipes, hand wipes, household cleaning wipes, industrial wipes and the like.

The solutions incorporated into conventional wet wipes include a variety of ingredients intended to enhance or impart particular properties to the wipe. The properties are related to items such as cleaning efficacy, fragrance, medication, reduced irritation, skin health, aesthetics and the like. For example, in baby wipes a solution providing a gentle soothing feeling without irritating the skin while maintaining cleaning and antimicrobial efficacy is desirable for product performance. Suitable ingredients used to provide these properties include, water, emollients, surfactants, preservatives, chelating agents, pH buffers or combinations thereof. Such solutions may also include lotions and/or medicaments.

It has been commonplace to use disposable wipes for a variety of cleaning and lubricating tasks. One example includes the current automotive wipes for use on the plastic and leather surfaces of a car's interior. There is a need in the art for an improved lubricating wipe which can, for example, clean, sharpen and lubricate garden tools, cutting blades, and skate blades. The downside of current oil based lubricating means involves the fact that the residual oil is not environmentally friendly and difficult for a common homeowner to dispose. In addition, the wipe substrate is typically contaminated with the residual oil/solvent.

In recent years, the consuming public has undertaken several environmentally friendly and/or green programs. These programs promote the use of environmentally friendly solutions and have necessitated the need for more environmentally friendly wipe designs. In addition, current lubricating methods include the use of solvents and mineral oils which often leave behind a slow or non-degradable carrier means. Thus, there is a need in the art for a wet wipe that allows the application of a lubricating means, but that allows the wipe to complete degrade the wipe portion with an environmentally friendly/green carrier solution and lubricating means.

SUMMARY OF INVENTION

The present invention generally relates to a biodegradable lubricating wipe, such as wet wipes. The wet wipes typically being fibrous sheet materials, pre-moistened with a solution for improved lubrication and/or protection of an area. In one embodiment the solution is comprised of a bio-based lubricant, a bio-based solvent and water. In one embodiment, the solution is comprised of mineral spirits and refined soybean oil. In another embodiment the solution is comprised of soy methyl ester and refined soybean oil. In yet another embodiment, the fibrous sheet material of the invention is biodegradable and the solution portion breaks down into a vaporizing component and a biodegradable carrier portion.

In one embodiment, the present invention relates to a wet wipe comprising: a fibrous sheet material; and a solution comprising a first portion and a second portion, wherein the first portion is a bio-based solvent and the second portion is a bio-based lubricant, wherein the fibrous sheet material is at least about 50 percent by weight biodegradable or compostable.

In another embodiment, the present invention relates to a wet wipe comprising: a fibrous sheet material that is biodegradable and/or compostable; and a solution comprising: about 80 percent by volume water; about 10 percent by volume alcohol; about 5 percent by volume refined soybean oil; about 3 percent by volume mineral spirits; and about 2 percent by volume binder additive, wherein the fibrous sheet material is impregnated with the solution.

In still another embodiment, the present invention relates to a wet wipe comprising: a fibrous sheet material that is biodegradable and/or compostable; and a solution comprising: from 0.1 percent by volume to about 99.9 percent by volume of at least one bio-based lubricant; and from 99.9 percent by volume to about 0.1 percent by volume of at least one first bio-based solvent.

DETAILED DESCRIPTION OF THE INVENTION

The present invention generally relates to a biodegradable lubricating wipe, such as wet wipes. The wet wipes typically being fibrous sheet materials, pre-moistened with a solution for improved lubrication and/or protection of an area. In one embodiment the solution is comprised of a bio-based lubricant, a bio-based solvent and water. In one embodiment, the solution is comprised of mineral spirits and refined soybean oil. In another embodiment the solution is comprised of soy methyl ester and refined soybean oil. In yet another embodiment, the fibrous sheet material of the invention is biodegradable and the solution portion breaks down into a vaporizing component and a biodegradable carrier portion. As used herein, the term "bio-based" means that a compound is either derived from a biological source (e.g., soybeans), is biodegradable, or both.

In one embodiment, the wipe portion of the present invention is formed from any suitable biodegradable or compostable material. Such materials include, but are not limited to, natural or synthetic biodegradable or compostable polymers (e.g., polycaprolactones, etc.), natural or synthetic biodegradable or compostable plant fibers (e.g., cellulose, cotton, paper, etc), any other natural or synthetic biodegradable or compostable fibrous material that can be formed into a woven and/or non-woven cloth-like structure, or combinations of two or more thereof. In one embodiment, the present invention generally relates to a wet wipe comprising fibrous material that can be formed into a woven and/or non-woven cloth-like structure and a solution which comprises a first portion and a second portion which are soluble in one another.

Materials used in wet wipes are well known to those skilled in the art. The wet wipes are typically made from fibrous sheet materials which may be woven or non-woven. For example, in one embodiment the wet wipes may include non-woven fibrous sheet materials which include melt blown, co-formed, air-laid, bonded-carded web materials, hydro-entangled materials, combinations thereof and the like. Such materials can compromise synthetic or natural fibers or combinations thereof, provided the material is at least about 50 percent by weight biodegradable or compostable, at least about 60 percent by weight biodegradable or compostable, at least about 70 percent by weight biodegradable or compostable, at least about 75 percent by weight biodegradable or compostable, at least about 80 percent by weight biodegradable or compostable, at least about 90 percent by weight biodegradable or compostable, at least about 95 percent by weight biodegradable or compostable, at least about 97.5 percent by weight biodegradable or compostable, or even at least about 99 percent by weight biodegradable or compostable. Here, as well as elsewhere in the specification and claims, individual numeric values can be combined to form non-disclosed ranges.

One of skill in the art would recognize that the term "wet wipes" cover a variety of applications, including, but not limited to: wet wipes, hand wipes, household wipes, industrial wipes and the like. The composition of the substrate of the wet wipe is typically made from a fibrous material which may be either woven or non-woven. In one embodiment the wet wipes of the present invention can be formed so as to have any desired basis weight. In another embodiment, the wet wipes of the present invention have a basis weight in the range of about 25 grams per square meter and about 120 grams per square meter, or from about 50 grams per square meter and about 110 grams per square meter, or from about 75 grams per square meter and about 100 grams per square meter, or even from about 80 grams per square meter and about 90 grams per square meter. Here, as well as elsewhere in the specification and claims, individual range limits can be combined to form additional non-disclosed ranges.

In one embodiment the wet wipe comprises a co-formed base sheet of polymeric microfibers and cellulosic fibers. In another embodiment the wet wipe comprises a composite which includes multiple layers of materials. For example, the wet wipes may include a three layer composite which includes an elastomeric film or melt-blown layer between two co-formed layers as described above. In another embodiment, the wet wipe is comprised completely from cellulosic materials.

The wet wipes of the present invention also contain solutions absorbed into the wet wipes. The amount of solutions contained within each wet wipe may vary depending on the type of material being used to provide the wet wipes, the type of solution being used, the type of container being used to store the wet wipes and the desired end use properties of the wet wipes. Any suitable amount of solution can be used in conjunction with the wet wipes of the present invention so long as they function as intended. In another embodiment, each wet wipe contains about 150 weight percent to about 600 weight percent solution based on the dry weight of the wipe.

In one embodiment, the solution that is used in conjunction with the wet wipes of the present invention is comprised of first portion that evaporates and a second portion that is biodegradable. In one embodiment, the second portion of the solution of the present invention should be stable enough to accomplish its intended goal (e.g., lubrication) but biodegrades within a suitable amount of time so as to not remain on a surface permanently. The first portion of the solution is, in one embodiment, designed to evaporate in a short amount of time (e.g., about 4 hours, about 8 hours, about 12 hours, about 24 hours, or even up to about 1 week). In one embodiment the solutions is comprised of mineral spirits and refined soybean oil. In another embodiment, the solution includes soy methyl ester and refined soybean oil. Suitable components of the solutions include, but are not limited to mineral spirits (CAS#8052-41-3) refined soybean oil (CAS#8001-22-7) and soy methyl ester.

The solution can also include a variety of other components which may assist in providing the desired wiping, cleaning and lubricating properties. For example the component may include water, emollients, surfactants, preservatives, chelating agents, pH buffers, fragrances, binders, or combinations thereof. The solution can also contain lotions, other solvents, or other carrier agents.

In another embodiment, the solution is comprised of three portions, a bio-based lubricant portion, a bio-solvent portion and an inert portion. These three portions are utilized at a variety of ranges to accomplish the intended goal (e.g., lubrication) but biodegrades within a suitable amount of time so as to not remain on a surface permanently.

The bio-based lubricant portion (also referred to as bio-oil) can be soybean oil, rape seed oil, corn oil, sunflower oil, palm kernel oil, coconut oil, cottonseed oil, olive oil, palm oil, peanut oil, safflower oil, sesame oil, nut oils, melon seed oils, gourd seed oils, flax seed oil, hemp oil, wheat germ oil, castor oil, rice bran oil, tung oil, other vegetable/fruit oils, animal fat (including tallow, lard, yellow grease and fish-oil), algae oil, copaiba, oil from halophytes, fungi and any combination of the same.

The bio-solvent portion (also referred to as a bio-based solvent) can be soy methyl ester, lactate esters (produced from processes using sugar, starches and oils and high performance microbial fermentation), and D-limonene (oils extracted from citrus rinds). Other suitable bio-based solvents can be derived from agricultural crops such as corn, soy beans, citrus fruit skins or tree barks. For example, ethyl lactate, methyl soyate, and terpenes (derived from corn, soybeans and citrus fruit peels respectively) can all be used in addition to pine oil. Of the previously listed bio-based solvents, these can be used individually or in combination of one or more of the same. The advantages to using bio-based solvents involve the lower environmental impact such as low toxicity, biodegradability, less VOC's being generated and less pollution during the refining processes versus petroleum based refining.

A table detailing the three components of one embodiment illustrates the various ratios in addition to examples of products which can be utilized (all units are approximations):

TABLE 1

| | Bio-Based Lubricant | Bio-Based Solvent | Alternative/ Additional Solvent |
|---|---|---|---|
| Range | 0.1 to 100 Percent By Volume | 0 to 99.9 Percent By Volume | 0 to 99.9 Percent By Volume |
| Examples | Soybean oil, rape seed oil, corn oil, sunflower oil, palm kernel oil, coconut oil, cottonseed oil, olive oil, palm oil, peanut oil, safflower oil, sesame oil, sunflower oil, nut oils, melon seed oils, gourd seed oils, flax seed oil, hemp oil, wheat germ oil, castor oil, rice bran oil, tung oil, other vegetable/fruit oils, animal fat, tallow, lard, yellow grease, fish-oil, algae oil, copaiba, oil from halophytes, fungi, or suitable mixtures of any two or more thereof. | Soy methyl ester, lactate esters, D-limonene, ethyl lactate, methyl soyate, terpenes, pine oil, or suitable mixtures of two or more thereof. | Water, alcohol, or any combination thereof. |

In the above embodiment, the solution can alternatively include the use of mineral spirits as a solvent. Said mineral spirits designed to evaporate in a short amount of time (e.g., about 4 hours, about 8 hours, about 12 hours, about 24 hours, or even up to about 1 week).

In various embodiments, one or more additives are added to control various properties of the solution. These properties include, but are not limited to: preventing the degradation of the refined soybean oil, retaining the mineral spirits, the soy methyl ester or the bio-solvent, preventing the premature release of the mineral spirits, the soy methyl ester or the bio-solvent, including one or more surfactants to act as emulsifiers or providing additional cleansing/lubricating properties, controlling the pH of the solution, formulating so as not to irritate a user's skin, formulating to act as a corrosion prevention means, including a disinfectant designed to kill or destroy potential undesired cross-contaminating microbes, controlling the thermal stability of the solution, controlling viscosity, controlling temperature ranges, controlling the ability to maintain its properties under extreme pressure wear and the use of detergents.

The wet wipes of the present invention can be manufactured using any suitable process technology as is known to those of skill in the art. The particular method and sequence of steps described herein is not to be construed in any manner as limiting. Rather, the following process is disclosed as one means of producing a wet wipe and a stack of wet wipes. Initially a supply roll of the material being converted into the wet wipes is unwound to provide a continuously moving web of material. The web of material is saturated or otherwise impregnated with the solution of the present invention by any suitable means such as spraying, dipping, or the like. In one embodiment, the web of material is passed over several perforated tubes which exude the solution into the material.

The web of material is slit in the machine direction into multiple ribbons, each of which may be folded into the type of fold desired for the individual wet wipe. The web of material is slit using a cutter as are well known to those of skill on the art. For example, the web of material can be slit into eight individual ribbons. The ribbons of material are then folded into a folded configuration such as a z-folded configuration. For example, each ribbon of material may define a top flap portion, a central portion and a bottom flap portion. The top and bottom flap portions are connected to and folded over and under the central portion, respectively to provide the z-folded configuration.

Each folded ribbon may then be combined, one ribbon on top of the other, with the other seven folded ribbons from the same web of material to form a continuous "sausage." The sausage is then cut into "clips" of eight wet wipes apiece and the clips of wet wipes are arranged in a stacked configuration. The number of clips in a stack depends on the desired number of stacks and the number of wet wipes in the final package. For example, for an 80-count package having one stack, ten clips of eight wet wipes apiece would be required to form a single stack of 80 wet wipes. After the stack of wet wipes is properly configured, it may be placed into the interior of a container, such as a plastic tub, to provide a package of wet wipes. The container provides a substantially hermetically sealed environment for the wet wipes to minimize the escape of any solution therefrom.

In one embodiment, a wet wipe according to the present invention comprises: a fibrous sheet material that is biodegradable and/or compostable; and a solution comprising: about 80 percent by volume water; about 10 percent by volume alcohol; about 5 percent by volume refined soybean oil; about 3 percent by volume mineral spirits; and about 2 percent by volume binder additive, wherein the fibrous sheet material is impregnated with the solution. In another embodiment, a wet wipe according to the present invention comprises: a fibrous sheet material that is biodegradable and/or compostable; and a solution comprising: about 90 percent by volume water; about 8 percent by volume refined soybean oil; and about 2 percent by volume mineral spirits, wherein the fibrous sheet material is impregnated with the solution.

In another embodiment, a wet wipe according to the present invention comprises: a fibrous sheet material that is biodegradable and/or compostable; and a solution comprising: from 0.1 percent by volume to about 99.9 percent by volume of at least one bio-based lubricant; and from 99.9 percent by volume to about 0.1 percent by volume of at least one first bio-based solvent. In one instance, the solution further comprises from about 0 to 99.9 percent by volume at least one second bio-based solvent (listed above in Table 1 as the alternative and/or additional solvent.

In one embodiment, the at least one first bio-based solvent is selected from one or more soy methyl esters, one or more lactate esters, D-limonene, ethyl lactate, methyl soyate, one or more terpenes, one or more pine oils, or suitable combinations of two or more thereof, and the at least one second bio-based solvent is selected from water, one or more alcohols, or suitable combinations of two or more thereof.

In one embodiment, the solution of the present invention's wet wipe comprises from about 2.5 percent by volume to about 95 percent by volume of at least one bio-based lubricant, and from about 97.5 percent by volume to about 5 percent by volume of at least one first bio-based solvent. In another embodiment, the solution of the present invention's wet wipe comprises from about 5 percent by volume to about 90 percent by volume of at least one bio-based lubricant, and from about 95 percent by volume to about 10 percent by volume of at least one first bio-based solvent. In still another embodiment, the solution of the present invention's wet wipe comprises from about 7.5 percent by volume to about 85 percent by volume of at least one bio-based lubricant, and from about 92.5 percent by volume to about 15 percent by volume of at least one first bio-based solvent. In still another embodiment, the solution of the present invention's wet wipe comprises from about 10 percent by volume to about 80 percent by volume of at least one bio-based lubricant, and from about 90 percent by volume to about 20 percent by volume of at least one first bio-based solvent. In still another embodiment, the solution of the present invention's wet wipe comprises from about 15 percent by volume to about 75 percent by volume of at least one bio-based lubricant, and from about 85 percent by volume to about 25 percent by volume of at least one first bio-based solvent. In still another embodiment, the solution of the present invention's wet wipe comprises from about 20 percent by volume to about 70 percent by volume of at least one bio-based lubricant, and from about 80 percent by volume to about 30 percent by volume of at least one first bio-based solvent. In still another embodiment, the solution of the present invention's wet wipe comprises from about 25 percent by volume to about 65 percent by volume of at least one bio-based lubricant, and from about 75 percent by volume to about 35 percent by volume of at least one first bio-based solvent. In still another embodiment, the solution of the present invention's wet wipe comprises from about 30 percent by volume to about 60 percent by volume of at least one bio-based lubricant, and from about 70 percent by volume to about 40 percent by volume of at least one first bio-based solvent. In still another embodiment, the solution of the present invention's wet wipe comprises from about 35 percent by volume to about 55 percent by volume of at least one bio-based lubricant, and from about 65 percent by volume to about 45 percent by volume of at least one first bio-based solvent. In still another embodiment, the solution of the present invention's wet wipe comprises from about 40 percent by volume to about 50 percent by volume of at least one bio-based lubricant, and from about 60 percent by volume to about 50 percent by volume of at least one first bio-based solvent. Here, as well as elsewhere in the specification and claims, individual range limits from different embodiments or ranges can be combined to form additional non-disclosed embodiments or ranges.

Although some of the features and concepts of the invention have been described in detail with particular reference to certain embodiments detailed herein, other embodiments which are within the scope of the invention can achieve the same results. Variations and modifications of the present invention which may be made by those skilled in the art are within the scope of the invention as defined by the claims and equivalents thereof.

What is claimed is:

1. A wet wipe comprising:
   a fibrous sheet material; and
   a solution comprising a first portion and a second portion, wherein the first portion is a solvent derived from agricultural crops and selected from soy methyl ester, ethyl lactate, or a suitable combination thereof, and the second portion is a vegetable oil, fruit oil, animal fat, algae oil, halophyte oil, or fungi oil lubricant, wherein the fibrous sheet material is at least about 50 percent by weight biodegradable or compostable, and wherein the solution comprises from about 5 percent by volume to about 90 percent by volume of the lubricant, and from about 95 percent by volume to about 10 percent by volume of the solvent.

2. The wet wipe of claim 1, wherein the fibrous sheet material is selected from hydro-entangled materials; melt-blown web materials; co-formed web materials; air-laid web materials and bonded carded web materials.

3. The wet wipe of claim 1, wherein the fibrous sheet material is a co-formed base sheet of polymeric microfibers and cellulosic fibers.

4. The wet wipe of claim 1, wherein the fibrous sheet material is multi-layered material formed from an elastomeric film or melt-blown layer disposed between two co-formed layers.

5. The wet wipe of claim 1, wherein the wipe contains about 150 weight percent to about 600 weight percent solution based on the dry weight of the wipe.

6. The wet wipe of claim 1, wherein the first portion of the solution evaporates and the second portion is biodegradable.

7. The wet wipe of claim 1, further comprising mineral spirits.

8. The wet wipe of claim 1, wherein the first portion is soy methyl ester and the second portion is refined soybean oil.

9. The wet wipe of claim 1, wherein the second portion of the solution is selected from one or more soybean oils, one or more rape seed oils, one or more corn oils, one or more sunflower oils, one or more palm kernel oils, one or more coconut oils, one or more cottonseed oils, one or more olive oils, one or more palm oils, one or more peanut oil, one or more safflower oils, one or more sesame oils, one or more nut oils, one or more melon seed oils, one or more gourd seed oils, one or more flax seed oils, one or more hemp oils, one or more wheat germ oils, one or more castor oils, one or more rice bran oils, one or more tung oils, one or more vegetable oils, one or more fruit oils, one or more animal fats, tallow, lard, yellow grease, one or more fish oils, one or more algae oils, copaiba, one or more oils from halophytes, one or more oils from fungi, or suitable combinations of two or more thereof.

10. The wet wipe of claim 1, wherein the solution further comprises water, one or more emollients, one or more surfactants, one or more preservatives, one or more chelating agents, one or more pH buffers, one or more fragrances, one or more lotions, one or more carrier agents, one or more disinfectants, one or more binders, or suitable combinations of two or more thereof.

11. The wet wipe of claim 1, wherein the solution further comprises a third portion which is inert.

12. The wet wipe of claim 1, wherein the solution further comprises an additional solvent.

13. The wet wipe of claim 12, wherein the additional solvent is one or more alcohols.

14. The wet wipe of claim 1, wherein the solution comprises from about 7.5 percent by volume to about 85 percent by volume of the lubricant, and from about 92.5 percent by volume to about 15 percent by volume of the solvent.

15. The wet wipe of claim 1, wherein the solution comprises from about 10 percent by volume to about 80 percent by volume of the lubricant, and from about 90 percent by volume to about 20 percent by volume of the solvent.

16. The wet wipe of claim 1, wherein the first portion is soy methyl ester and the second portion is soybean oil, and further comprising mineral spirits.

17. A wet wipe comprising:
    a fibrous sheet material; and
    a solution comprising a first portion and a second portion, wherein the first portion is a solvent derived from agricultural crops and selected from soy methyl ester, ethyl lactate, or a suitable combination thereof, and the second portion is a vegetable oil, fruit oil, animal fat, algae oil, halophyte oil, or fungi oil lubricant, wherein the fibrous sheet material is at least about 50 percent by weight biodegradable or compostable, and wherein the first portion is present in an amount of at least about 20% by volume and the second portion is present in an amount of at least 2.5% by volume.

18. A wet wipe comprising:
    a fibrous sheet material that is at least about 50 percent by weight biodegradable or compostable; and a solution comprising about 40% to about 50% soybean oil, about 50% to about 60% of soy methyl ester, and a preservative.

19. A wet wipe comprising:
a fibrous sheet material; and
a solution comprising a first portion and a second portion, wherein the first portion is a solvent derived from agricultural crops comprising soy methyl ester, ethyl lactate, or a suitable combination thereof and is present in an amount of at least about 10%, and the second portion is a vegetable oil, fruit oil, animal fat, algae oil, halophyte oil, or fungi oil lubricant and is present in at least about 2.5% by volume, and wherein the fibrous sheet material is at least about 50 percent by weight biodegradable or compostable.

20. A wet wipe comprising:
a fibrous sheet material; and
a solution comprising a first portion and a second portion, wherein the first portion is a solvent derived from agricultural crops comprising soy methyl ester, ethyl lactate, or a suitable combination thereof, and is present in at least about 20% by volume, and the second portion is a vegetable oil, fruit oil, animal fat, algae oil, halophyte oil, or fungi oil lubricant, and wherein the fibrous sheet material is at least about 50 percent by weight biodegradable or compostable.

21. A wet wipe comprising:
a fibrous sheet material that is biodegradable and/or compostable; and
a solution comprising:
from about 2.5 percent by volume to about 90 percent by volume of at least one vegetable oil, fruit oil, animal fat, algae oil, halophyte oil, or fungi oil lubricant; and
from about 97.5 percent by volume to about 10 percent by volume of at least one solvent derived from agricultural crops, the solvent comprising soy methyl ester, ethyl lactate, or a suitable combination thereof.

22. A wet wipe comprising:
a fibrous sheet material that is biodegradable and/or compostable; and
a solution comprising:
from about 0.1 percent by volume to about 80 percent by volume of at least one vegetable oil, fruit oil, animal fat, algae oil, halophyte oil, or fungi oil lubricant; and
from about 99.9 percent by volume to about 20 percent by volume of at least one solvent derived from agricultural crops, the solvent comprising soy methyl ester, ethyl lactate, or a suitable combination thereof.

23. The wet wipe of claim 17, wherein the lubricant is present in an amount from about 2.5 percent by volume to about 80 percent by volume, and wherein the solvent is present in an amount from about 97.5 percent by volume to about 20 percent by volume.

24. A method of cleaning a surface comprising contacting the wipe of claim 1 to a surface comprising a substance, and removing the substance from the surface.

25. A method of cleaning a surface comprising contacting the wipe of claim 17 to a surface comprising a substance, and removing the substance from the surface.

* * * * *